US008355785B1

(12) United States Patent
Hammond et al.

(10) Patent No.: US 8,355,785 B1
(45) Date of Patent: Jan. 15, 2013

(54) IMPLANTABLE PULSE GENERATOR INCLUDING AN INTEGRATED BLOCK FEEDTHRU AND HEADER ASSEMBLY

(75) Inventors: Nicholas Hammond, San Luis Obispo, CA (US); Narendra Nayak, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 1501 days.

(21) Appl. No.: 11/850,961

(22) Filed: Sep. 6, 2007

(51) Int. Cl.
*A61N 1/372* (2006.01)
(52) U.S. Cl. .......................................................... 607/37
(58) Field of Classification Search ...................... 607/37
See application file for complete search history.

(56) References Cited

U.S. PATENT DOCUMENTS

| | | | |
|---|---|---|---|
| 4,262,673 A * | 4/1981 | Kinney et al. | 607/5 |
| 4,715,380 A | 12/1987 | Harris | |
| 5,545,189 A * | 8/1996 | Fayram | 607/37 |
| 6,505,073 B2 * | 1/2003 | Gramse | 607/37 |
| 7,340,305 B2 * | 3/2008 | Fischbach et al. | 607/36 |

* cited by examiner

*Primary Examiner* — Christopher D Koharski
*Assistant Examiner* — Jeremiah Kimball

(57) ABSTRACT

An implantable pulse generator is disclosed herein. In one embodiment, the implantable pulse generator includes a housing, a feedthru, and a header. The housing includes an electronic component housed within the housing. The feedthru is mounted on the housing and includes an electrical insulator and a lead connector block. The electrical insulator includes a header face and a housing face opposite the header face. The lead connector block extends from the header face of the electrical insulator. The housing face faces in the general direction of the electronic component. The lead connector block is in electrical communication with the electronic component. The header includes an electrically insulative barrier and an outer covering. The electrically insulative barrier includes a feedthru face and a cavity. The feedthru face abuts the header face and the lead connector block resides in the cavity. The outer covering extends over the electrically insulative barrier.

17 Claims, 7 Drawing Sheets

IMPLANTABLE PULSE GENERATOR INCLUDING AN INTEGRATED BLOCK FEEDTHRU AND HEADER ASSEMBLY

FIELD OF THE INVENTION

The present invention relates to medical apparatus and methods of manufacturing such apparatus. More specifically, the present invention relates to implantable pulse generators and methods of manufacturing pulse generators.

BACKGROUND OF THE INVENTION

Current implantable pulse generators (e.g., pacemakers, defibrillators or implantable cardioverter defibrillators ("ICD")) employ header/feedthru designs that are difficult to assemble. For example, as shown in FIG. 1, which is an isometric view of a feedthru/header assembly 5 of a prior art ICD 10, eight feedthru wires 15 extend through the ICD housing 17 via ceramic insulators 20 to couple to connector blocks 25. Four wires 15 pass through each small circular insulator 20. During assembly, each wire 15 must be inserted through its respective insulator 20 and then formed such that it can reach its respective connector block 25 without being too close to adjacent wires 15, adjacent blocks 25 or the ICD housing 17. Each wire 15 is then welded to its respective connector block 25.

As can be understood from FIG. 1, should spacing be insufficient between adjacent wires 15, between a wire 15 and an adjacent block 25, or between a wire 15 and the ICD housing 17, a short can occur and lead to catastrophic failure of the ICD 10. Thus, the assembly difficulty and shorting potential associated with current ICD header/feedthru assembly designs results in manufacturing costs and failure rates that are higher than desired. Manufacturing costs are further increased by the use of platinum for the wires 15.

Once each wire 15 is welded to its respective block 25, a header 30, which is shown in phantom line, is cast about the wires 15 and blocks 25. However, as can be understood from FIG. 1, the wires 15 and blocks 25 combine to form complex and cumbersome geometries that can lead to air voids within the formed header 30. Such voids require drilling and filling in order to reduce the likelihood of a short occurring across the void. Such rework unnecessarily increases manufacturing costs. Additionally, due to the large amount of material that must be cast to encompass the wires 15 and blocks 25 and form the header 30, curing times for the cast material can be substantial, further increasing manufacturing costs.

There is a need in the art for a feedthru/header assembly with increased reliability and decreased manufacturing costs. There is also a need in the art for a method of manufacturing such a feedthru/header assembly.

SUMMARY

An implantable pulse generator is disclosed herein. In one embodiment, the implantable pulse generator includes a housing, a feedthru, and a header. The housing includes an electronic component contained within the housing. The feedthru is mounted on the housing and includes an electrical insulator and a lead connector block. The electrical insulator includes a header face and a housing face opposite the header face. The lead connector block extends from the header face of the electrical insulator. The housing face faces in the general direction of the electronic component inside the housing. The lead connector block is in electrical communication with the electronic component. The header includes an electrically insulative barrier and an outer covering. The electrically insulative barrier includes a feedthru face and a block cavity. The feedthru face abuts the header face and the lead connector block resides in the cavity. The outer covering extends over the electrically insulative barrier.

A method of manufacturing an implantable pulse generator is disclosed herein. In one embodiment, the method includes: providing a housing; locating an electronic component within the housing; providing an electrical insulator including a header face and an housing face opposite the header face; joining a lead connector block to the header face such that the lead connector block extends from the header face; mounting the electrical insulator on the housing such that the housing face faces in the general direction of the electronic component; electrically coupling the lead connector block to the electronic component; extending an electrically insulative barrier over the header face such that the lead connector block is received in an opening in the electrically insulative barrier; and extending an outer cover over the electrically insulative barrier.

A header/feedthru assembly for an implantable pulse generator is disclosed herein. In one embodiment, the assembly includes a feedthru and a header. The feedthru includes an electrical insulator and a lead connector block. The electrical insulator includes a header side and a pulse generator side opposite the header side. The lead connector block is near the header side. The header includes an electrically insulative barrier and a covering extending over the electrically insulative barrier. The electrically insulative barrier extends over the header side.

A method of manufacturing a header/feedthru assembly for an implantable pulse generator is disclosed herein. In one embodiment, the method includes: providing an electrical insulator including a header side and a pulse generator side opposite the header side; operably coupling a lead connector block to the header side; placing an electrically insulative barrier over the header side; and extending a covering over the electrically insulative barrier.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
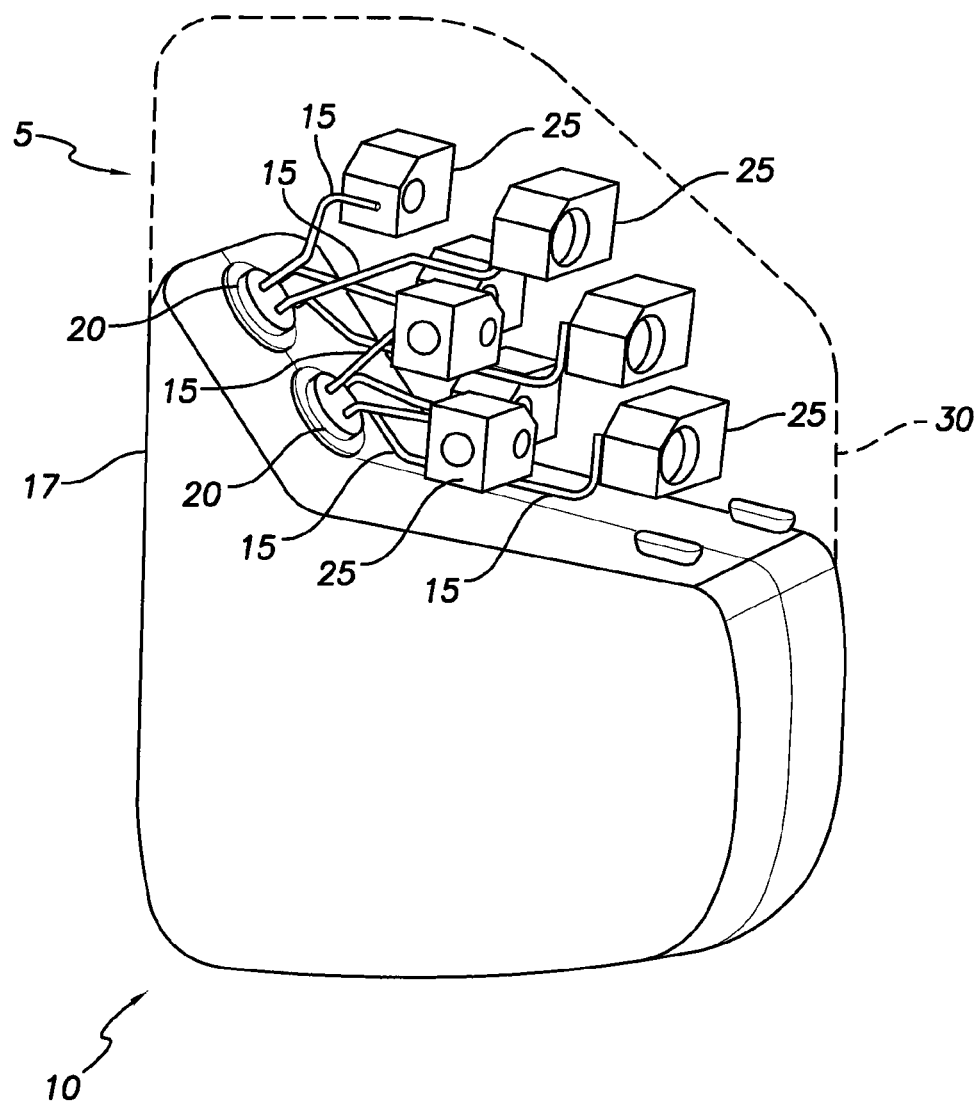
FIG. 1 is an isometric view of a feedthru/header assembly of a prior art ICD.

A feedthru/header assembly 50 for an implantable pulse generator (e.g., pacemaker, defibrillator, or implantable cardioverter defibrillator ("ICD")) 55 and a method of manufacturing such an assembly 50 are disclosed herein. In one embodiment, the feedthru/assembly 50 includes a feedthru 60 and a header 65. The feedthru 60 includes an electrical insulator 70 and a plurality of lead connector blocks 75 abutting against, and extending from, a header side 80 of the electrical insulator 70. This configuration for the feedthru 60 substantially simplifies manufacturing and improves reliability by reducing the likelihood of a short.

The header 65 includes an electrically insulative barrier 85 and a header cover 90 extending over the electrically insulative barrier 85. The electrically insulative barrier 85 includes a feedthru face 95 with block receiving cavities or openings 170 defined therein for receiving the lead connector blocks 75 when the feedthru face 95 abuts against the header face 80. This header configuration further simplifies manufacturing, reduces curing time, and reduces the likelihood of a short by improving the robustness of the header 65.

Figure 2:
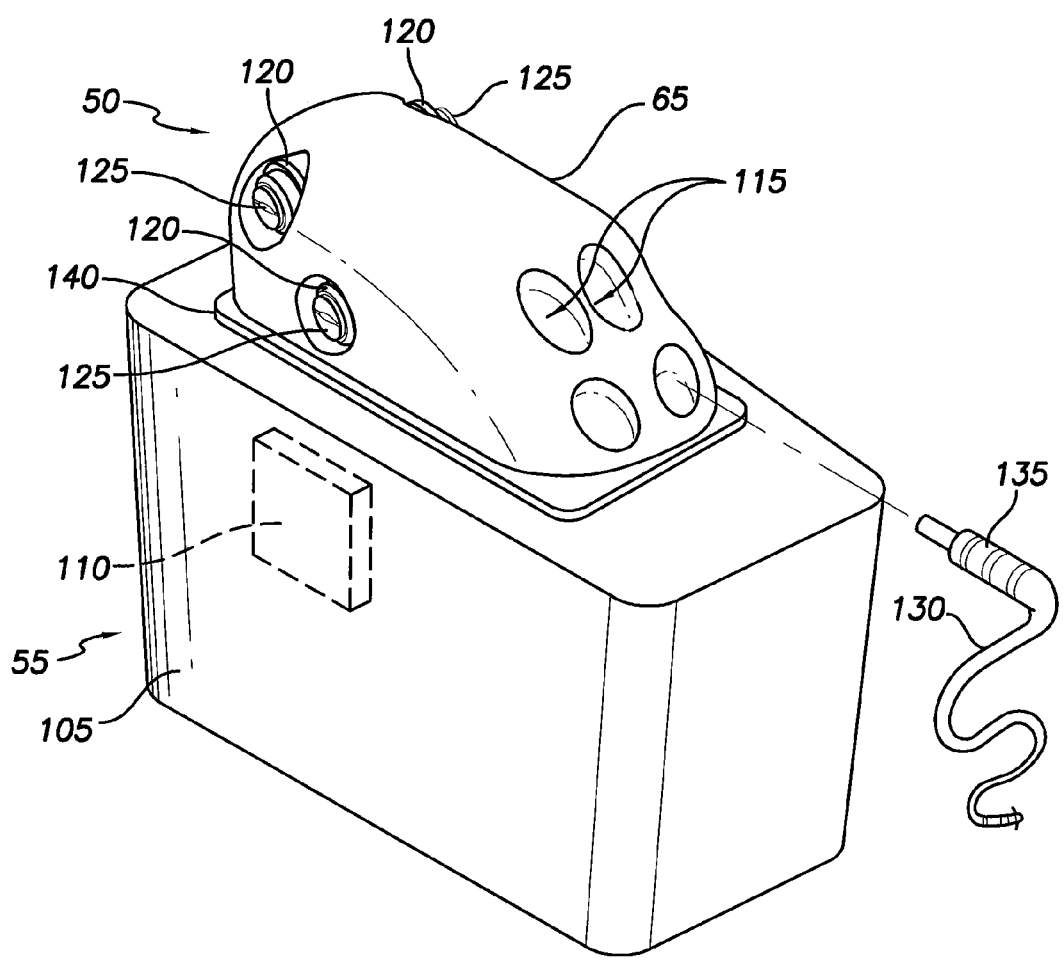
FIG. 2 is an isometric view of a feedthru/header assembly mounted on a generator.

For a detailed discussion regarding the feedthru/assembly 50 and its relationship to the implantable pulse generator 55, reference is made to FIG. 2, which is an isometric view of the assembly 50 mounted on the generator 55. As shown in FIG. 2, the generator 55 includes a housing 105 enclosing the various electronic components 110 (shown in phantom line) of the generator 55. For example, in the context of an ICD 55, the electronic components 110 will include an ICD hybrid 110.

As indicated in FIG. 2, the assembly 50 is mounted on the housing 105 and includes lead connector cavities 115 and lead anchor setscrew assemblies 120 covered by polymer septums 125. To connect an implantable lead 130 to the generator 55, the lead connector end 135 of the implantable lead 130 is received in its respective lead connector cavity 115. A tool is used to tighten the lead anchor setscrew assemblies 120 to retain the lead connector end 135 in its respective cavity 115 and achieve electrical contact between the lead connector end 135 and the block 75. In one embodiment, contact springs are substituted for the lead anchor setscrew assemblies 120 to establish electrical contact between the lead end 135 and the block 75 being coupled to the lead end 135.

In one embodiment, the upper pair of cavities 115 will be DF-1 connector cavities, and the lower pair of cavities 115 will be IS-1 connector cavities 115. In one embodiment, the assembly 50 will include a greater or lesser number of cavities 115. In one embodiment, one or more of the connector cavities 115 will be IS-4 cavities 115. In one embodiment, the front pair of short blocks 75 is IS-1 ring blocks, the middle pair of short blocks 75 is IS-1 tip blocks, and the rear pair of tall blocks 75 is DF-1 blocks.

Figure 3:
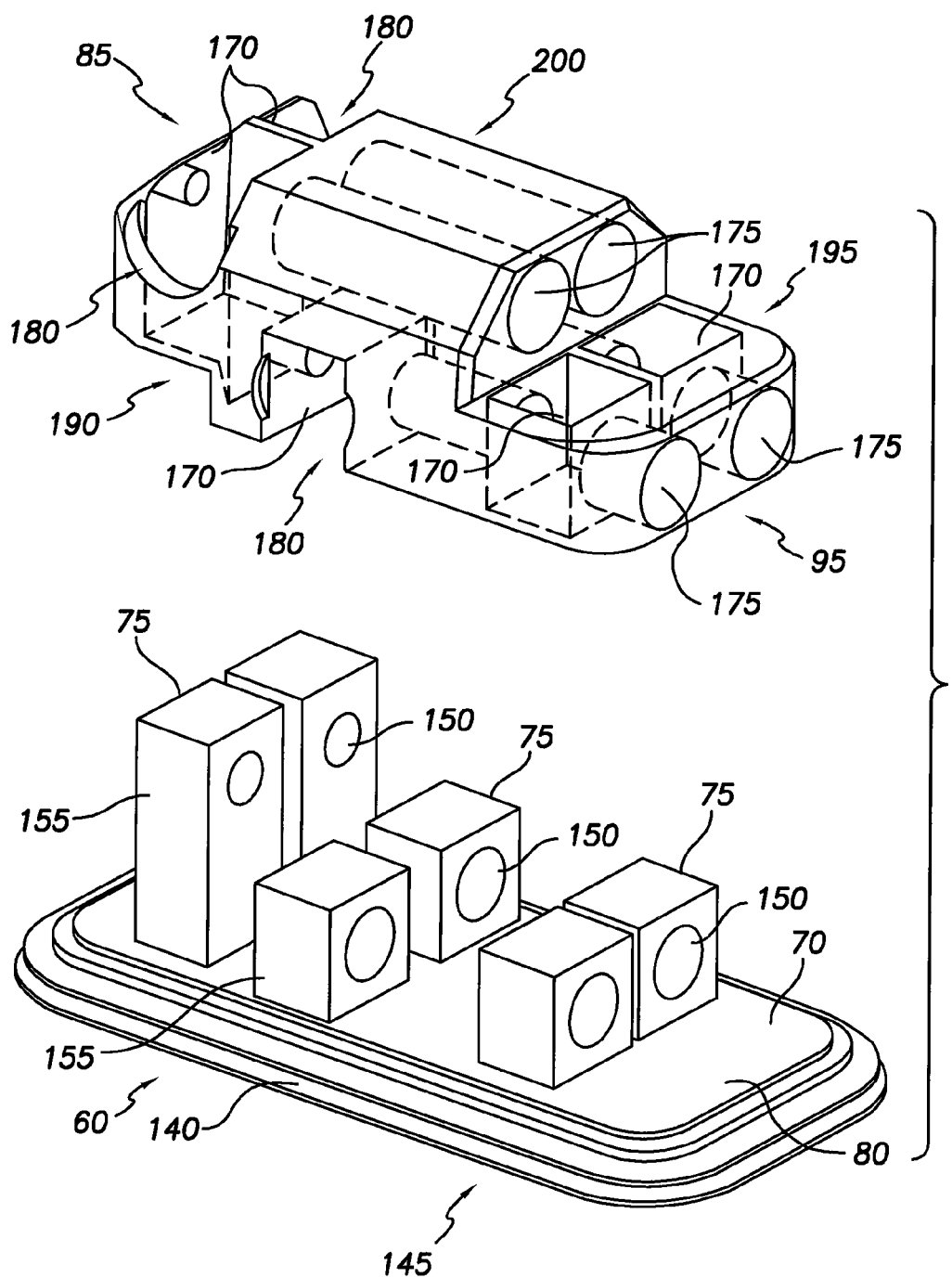
FIG. 3 is an exploded isometric view of a portion of the feedthru/header assembly.
Figure 4:
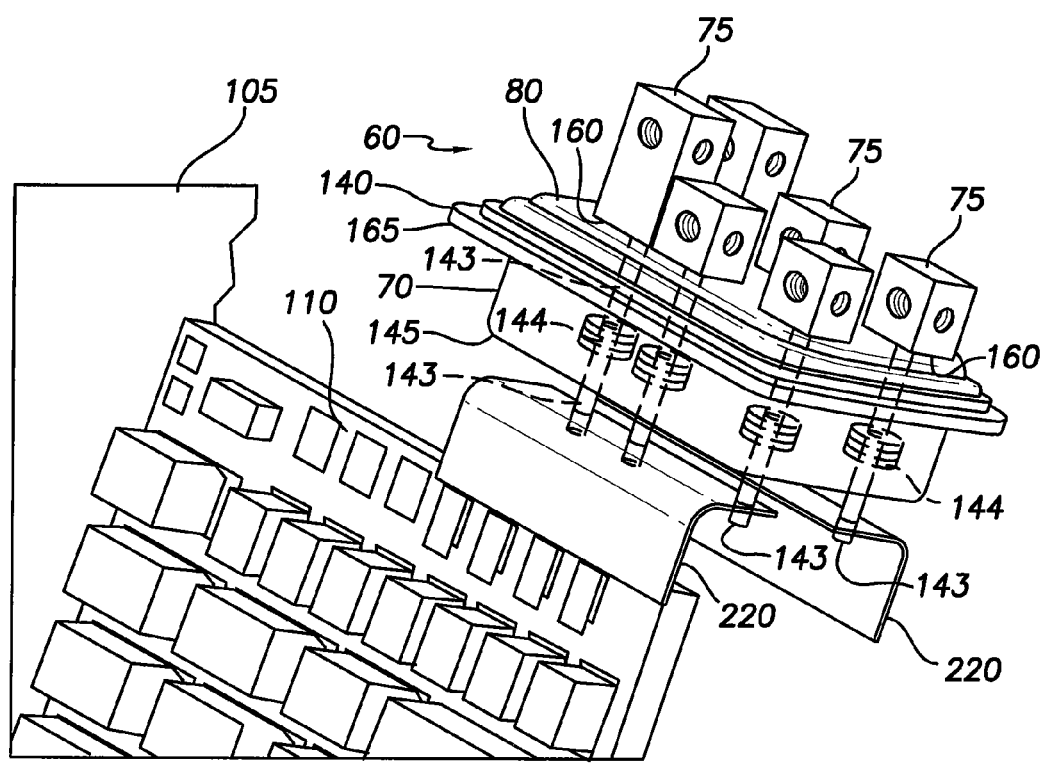
FIG. 4 is an isometric view of the feedthru electrically coupled to an electronic component (e.g., an ICD hybrid) located within the housing of the pulse generator.

For a detailed discussion of the feedthru 60 of the feedthru/header assembly 50, reference is made to FIGS. 3 and 4. FIG. 3 is an exploded isometric view of a portion of the feedthru/header assembly 50. FIG. 4 is an isometric view of the feedthru 60 electrically coupled to an electronic component 110 (e.g., an ICD hybrid) located within the housing 105 of the pulse generator 55.

As indicated in FIGS. 3 and 4, the feedthru 60 includes an electrical insulator 70, lead connector blocks 75, a flange 140, conductors 143 and a capacitor or other EMI filtering element 144. In one embodiment, the electrical insulator 70 extends between the inner boundaries of the flange 140 in a generally continuous manner. The electrical insulator 70 includes a header side 80 and a pulse generator side 145 opposite the header side 80. In one embodiment, the electrical insulator 70 is formed of a ceramic material such as Glass Seal, Kryoflex, or etc.

As illustrated in FIGS. 3 and 4, in one embodiment, the flange 140 extends about the outer edge of the electrical insulator 70. In one embodiment, the flange 140 is formed of titanium. In other embodiments, the flange 140 is formed of other metal materials such as stainless steel, MP35N, or etc.

As depicted in FIGS. 3 and 4, the lead connector blocks 75 extend directly from the header side 80 of the electrical insulator 70. Each block 75 includes an opening 150 for receiving a lead connector end 135. Some blocks 75 also include openings 155 for receiving lead anchor setscrew assemblies 120. In one embodiment, the lead connector blocks 75 are formed of a metal material such as titanium, stainless steel, MP35N, or etc. In one embodiment, the blocks 75 are machined or metal injection molded.

As shown in FIG. 4, in one embodiment, a conductor 143 extends from a bottom surface 160 of each lead connector block 75 to an electrical component 110. In one embodiment, the conductors 143 are wires, posts, cables or other configurations formed of a metal material such as platinum-iridium alloy, titanium, palladium, stainless steel, or etc. In one embodiment, each conductor 143 is attached to its respective block 75 prior to the block 75 being attached to the electrical insulator 70. In one embodiment, a conductor 143 is formed with a block 75 to be an integral extension of the block 75. In one embodiment, a conductor 143 is formed separate from a block 75 and then joined to the block 75 via brazing, welding, soldering, adhesive bonding, mechanical fastening (e.g., crimping, threading, clips, etc.), or etc. to form an integral assembly.

Figure 5:
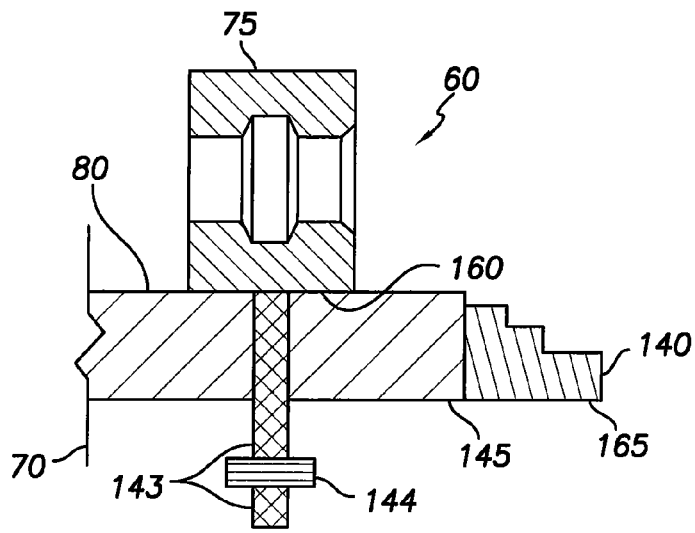
FIG. 5 is a vertical cross-section taken through a lead connector block, conductor, electrical insulator and flange, in one embodiment.
Figure 6:
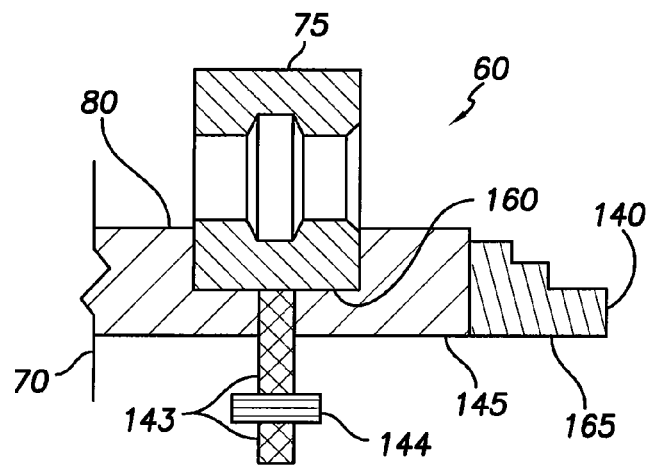
FIG. 6 is a vertical cross-section taken through a lead connector block, conductor, electrical insulator and flange, in one embodiment.
Figure 7:
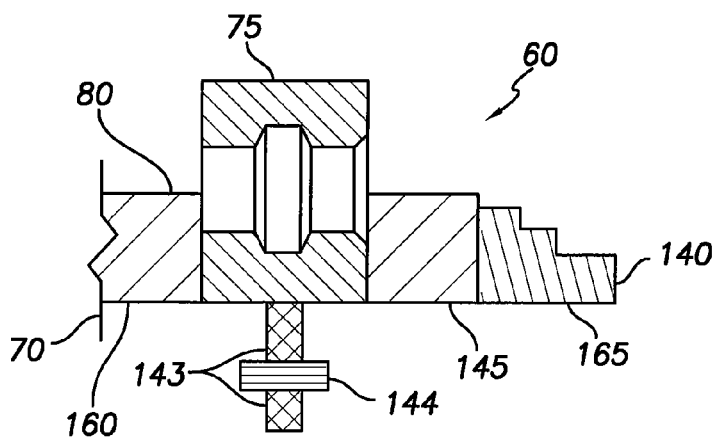
FIG. 7 is a vertical cross-section taken through a lead connector block, conductor, electrical insulator and flange, in one embodiment.

As illustrated in FIGS. 4-7, in one embodiment, a discoidal capacitor 144 is connected to each conductor 143 to form an EMI filter. As shown in FIG. 4, in one embodiment, the capacitors 144 are imbedded in the electrical insulator 70. As indicated in FIGS. 5-7, in one embodiment, the capacitors are located outside and below the electrical insulator 70. In one embodiment, the capacitors 144 couple directly to, or are an integral part of, the blocks 75.

For a discussion of the relationship between the blocks 75, conductors 143 and the electrical insulator 70, reference is made to FIGS. 5-7, which are various embodiments of the feedthru 60 shown in vertical cross-section taken through a lead connector block 75, a conductor 143, the electrical insulator 70 and the flange 140. As illustrated in FIG. 5, in one embodiment, the bottom surface 160 of a lead connector block 75 sits flush against the header surface 80 of the electrical insulator 70, and the block 75 extends upwardly from the header surface 80. The conductor 143 extends from the block bottom surface 160, through the electrical insulator 70 out of the generator side 145 of the insulator 70. In one embodiment, the block bottom surface 160 is adhesively bonded, brazed or otherwise securely attached to the header surface 80.

As indicated in FIG. 6, in one embodiment, the bottom surface 160 of a lead connector block 75 is recessed within the electrical insulator 70 such that the block 75 extends through the header surface 80 of the insulator 70. The block 75 extends upwardly from the header surface 80. The conductor 143 extends from the block bottom surface 160, through the electrical insulator 70 and out of the generator side 145 of the insulator 70. In one embodiment, the lead connector block 75 is insert molded into the electrical insulator 70. In other embodiments, the block 75 is adhesively bonded, brazed or otherwise securely attached within the electrical insulator 70.

As indicated in FIG. 7, in one embodiment, the bottom surface 160 of a lead connector block 75 is recessed within the electrical insulator 70 such that the block bottom surface 160 is flush with, or extends through, the generator surface 145 of the insulator 70. The block 75 extends upwardly from the header surface 80. The conductor 143 extends downward from the block bottom surface 160. In one embodiment, the lead connector block 75 is insert molded into the electrical insulator 70. In other embodiments, the block 75 is adhesively bonded, brazed or otherwise securely attached within the electrical insulator 70.

As can be understood from FIG. 4, in one embodiment, the electrical insulator 70 will extend downwardly past the flange bottom surface 165 to a greater or lesser extent. As can be understood from FIGS. 5-7, in one embodiment, the generator surface 145 of the electrical insulator 70 will be generally flush with the flange bottom surface 165. In other embodiments, the generator surface 145 of the electrical insulator 70 will be recessed a greater or lesser amount relative to the flange bottom surface 165.

As can be understood from FIGS. 3-7, the configuration of the feedthru 60 is advantageous for several reasons. First, the feedthru 60 does not require conductor wires to be routed on the header side 80 of the electrical insulator 70, thereby eliminating much of the manufacturing difficulty and potential for electrical shorting associated with prior art feedthrus. Second, the blocks 75 make flush contact with the header side 80 of the electrical insulator 70. In other words, the blocks 75 are connected to the electrical insulator 70 such that voids or cavities not exist between the blocks 75 and the header surface 80 of the insulator 70. As a result, the feedthru configuration allows for the use of an electrically insulative barrier 85, which is discussed next and reduces the likelihood of having to rework the header 65 due to the formation of voids in the header 65. Third, the insulator 70, blocks 75, flange 140, conductors 143 and capacitors 144 combine to form a one-piece integral feedthru 60, which simplifies assembly. Fourth, the electrical path formed by the blocks 75 and conductors 143 provides reduced electrical resistance by decreasing the length and increasing the cross-sectional area of the electrical path as compared to the electrical path formed by the blocks 25 and wires 15 of FIG. 1.

Figure 8:
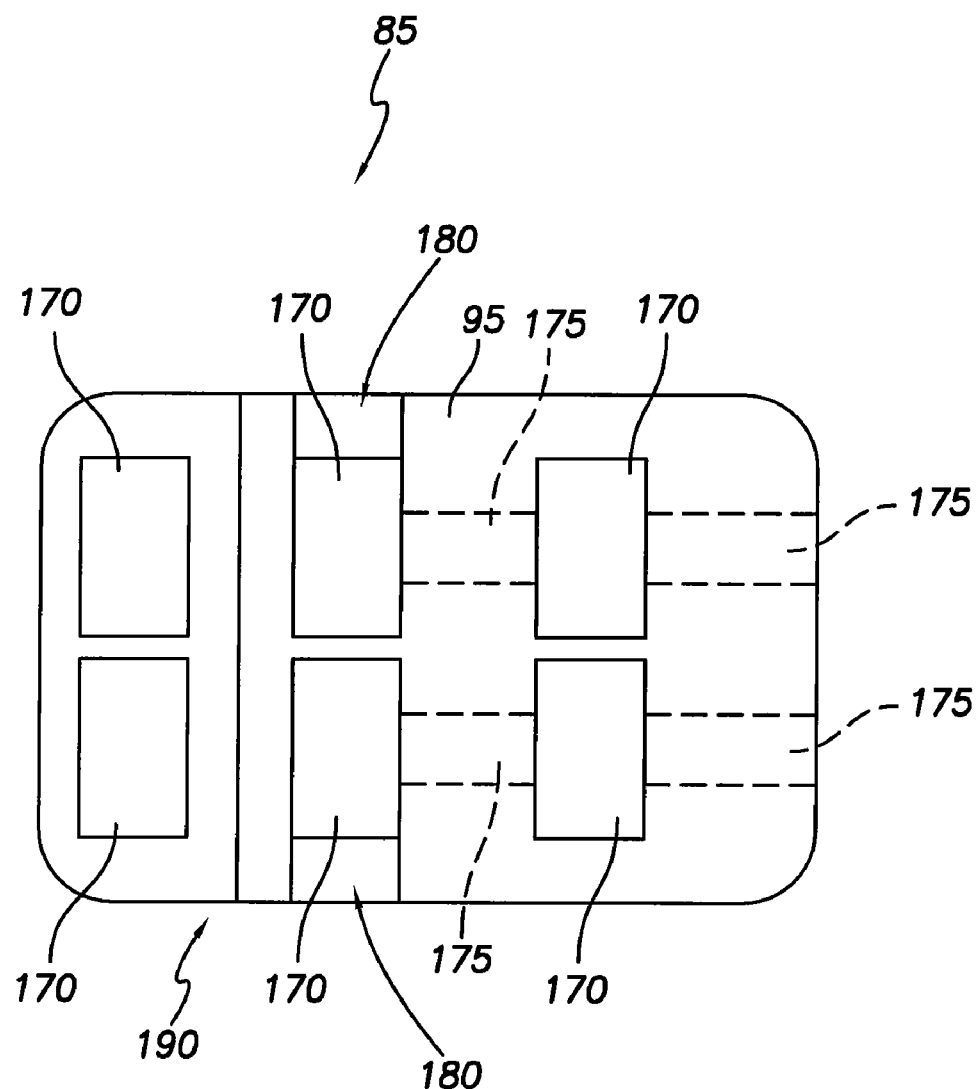
FIG. 8 is a bottom view of the electrically insulative barrier.

For a discussion of the electrically insulative barrier 85, reference is made to FIG. 3 and to FIG. 8. FIG. 8 is a bottom view of the electrically insulative barrier 85. As shown in FIGS. 3 and 8, the electrically insulative barrier 85 includes block receiving cavities 170, lead connector receiving bores 175, anchor assembly or septum cutouts 180 and a feedthru face 95.

In one embodiment, the feedthru face 95 is generally planar and extends nearly continuously and uninterrupted the full length and width of the electrically insulative barrier 85, with the exception of block cavities 170 opening through the feedthru face 95 and a step 190 near the rear of the electrically insulative barrier 85. As indicated in FIG. 3, in one embodiment, the forward and rear pairs of block cavities 170 vertically extend completely through the electrically insulative barrier 85, and the middle pair of block cavities 170 vertically extend through the feedthru face 95, only. The septum cutouts 180 horizontally extend through the sidewalls of the electrically insulative barrier 85 adjacent the rear and middle pairs of block cavities 170.

As illustrated in FIG. 3, in one embodiment, a pair of lead connector bores 175 extends horizontally from the front of the electrically insulative barrier 85 to connect the front and middle pairs of block cavities 170. A step 195 extends over the front pair of block cavities 170. A pair of lead connector bores 175 extends horizontally through a hump or domed portion 200 of the electrically insulative barrier 85 and over the middle pair of block cavities 170 from the step 195 to the rear pair of block cavities 170.

In one embodiment, the electrically insulative barrier 85 is formed of a polymer material such as polysulfone, Tecothane, Delrin, or etc. In one embodiment, the polymer material is molded, machined or otherwise formed. In one embodiment, the electrically insulative barrier 85 is formed of a ceramic material such as Glass Seal, or etc.

Figure 9:
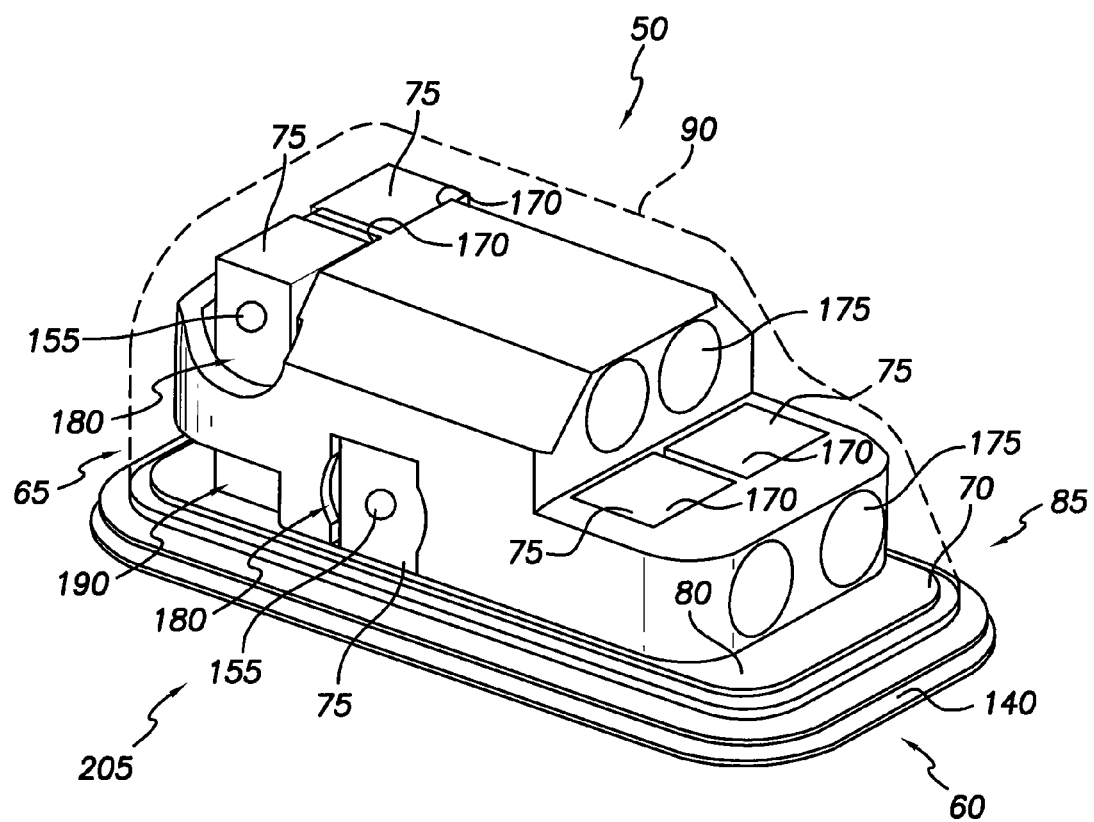
FIG. 9 is an isometric view of the electrically insulative barrier matingly mounted on the feedthru.

For a discussion of mating relationship between the feedthru 60 and the electrically insulative barrier 85, reference is made to FIG. 9, which is an isometric view of the electrically insulative barrier matingly mounted on the feedthru 60. As illustrated in FIG. 9, each lead connector block 75 of the feedthru 60 is received in its respective block receiving cavity 170 of the electrically insulative barrier 85. In one embodiment, configuration and tolerances of the cavities 170 are such that little, if any, space exists between a connector block 75 and the walls of its respective block cavity 170. When each connector block 75 is fully received in its respective block cavity 170, the planar feedthru face 95 of the electrically insulative barrier 85 abuts in a generally flush manner with the planar header face 80 of the feedthru 60 such that generally no space exits between the two surfaces 80, 95. Also, when each connector block 75 is fully received in its respective block receiving cavity 170, each septum cutout 180 aligns with its respective anchor screw location 155.

As can be understood from FIGS. 1 and 9, during manufacture and shipping of the feedthru/header assembly 50 and during deployment of the generator 55 and assembly 50 within a patient, the electrically insulative barrier 85 provides and maintains a generally rigid separation/isolation and support between adjacent blocks 75 and between blocks 75 and the generator housing 105. As a result, there is a decreased likelihood of electrical short between adjacent blocks 75 or between a block 75 and the generator housing 105.

As can be understood from FIG. 9, the feedthru 60 and electrically insulative barrier 85 combine into a configuration or assembly 205 that is generally block-like with relatively simply geometry. Also, there is close mating conformity between the blocks 75 and their respective cavities 170 and between the faces 80, 95. As a result of the simple geometry of the assembly 205 and the mating conformity between elements of the electrically insulative barrier 85 and the feedthru 60, the combined feedthru/electrically insulative barrier assembly 205 depicted in FIG. 9 presents little, if any, opportunity for the formation of turbulence or air pockets when the header outer housing 90 (shown in phantom line) is formed about the combined feedthru/electrically insulative barrier assembly 205, as described later in this Detailed Description.

As can be understood from FIGS. 1 and 9, the header portion 65 of the header/feedthru assembly 50 extends over the feedthru 60 and includes the electrically insulative barrier 85 and the outer housing 90. In one embodiment, the feedthru/ electrically insulative barrier assembly 205, and more specifically, the connector blocks 75 and the electrically insulative barrier 85 accounts for a substantial majority of the volume of the header/feedthru assembly 50. In other words, the material forming the outer housing 90 accounts for a relatively small minority of the volume defined between the outer surface of the outer housing 90 and the header surface 80 of the electrical insulator 70. As a result, when the outer housing 90 is formed over the feedthru/block assembly 205, a relatively small amount of material is needed to form the outer housing 90. Accordingly, cure times for the outer housing material are reduced, and the likelihood of void formation is reduced.

In one embodiment, the outer housing 90 is formed over the feedthru/block assembly 205 via injection molding, casting, or etc. In one embodiment, the outer housing 90 is formed of a polymer material such as Tecothane, hysol epoxy, or etc.

In one embodiment, the material of the outer housing 90 accounts for between approximately 20 percent and approximately 40 percent of the volume defined between the outer surface of the outer housing 90 and the header surface 80 of the electrical insulator 70. In one embodiment, the material of the outer housing 90 accounts for less than approximately 15 percent of the volume defined between the outer surface of the outer housing 90 and the header surface 80 of the electrical insulator 70.

As can be understood from FIGS. 1, 3, 4 and 9, in one embodiment, the electrically insulative barrier 85 is placed over the feedthru 60 such that the connector blocks 75 are received in their respective cavities 170. The outer housing 90 is then molded, cast or otherwise formed directly over the feedthru/electrically insulative barrier assembly 205. The conductors 143 are electrically coupled to the electronic components 110 via soldering, brazing, welding a flex 220 (see FIG. 4), or etc. The flange 140 is then welded to the housing 105 of the generator 55 to form a hermetic seal, and no backfilling is required.

Although the present invention has been described with reference to preferred embodiments, persons skilled in the art will recognize that changes may be made in form and detail without departing from the spirit and scope of the invention.

What is claimed is:

1. An implantable pulse generator comprising:
   a housing comprising an electronic component housed within the housing; and
   a feedthru mounted on the housing and including an electrical insulator and a lead connector block, wherein the electrical insulator includes a header face and a housing face opposite the header face, the lead connector block extends from the header face of the electrical insulator, the housing face faces in the general direction of the electronic component, and the lead connector block is in electrical communication with the electronic component and comprises a plurality of spaced apart lead connectors mounted on the electrical insulator;
   wherein the feedthru further comprises a preformed, electrically insulative barrier that defines a plurality of recesses configured to receive respective ones of the lead connectors therewithin; and
   a header formed over the feedthru and electrically insulative barrier.

2. The generator of claim 1, further comprising a flange extending about an edge of the electrical insulator.

3. The generator of claim 2, wherein the flange is connected to the housing.

4. The generator of claim 1, wherein the lead connector block abuts against the header face.

5. The generator of claim 4, wherein a surface of the lead connector block is bonded, brazed or otherwise affixed to the header face.

6. The generator of claim 1, wherein a portion of the lead connector block is imbedded in the electrical insulator.

7. The generator of claim 1, wherein a portion of the lead connector block extends through the electrical insulator.

8. The generator of claim 1, wherein the lead connector block includes a DF-1, IS-1 or IS-4 cavity.

9. The generator of claim 1, further comprising a capacitor electrically coupled to the lead connector block and wherein the capacitor forms an EMI filter.

10. The generator of claim 9, wherein the capacitor is imbedded in the electrical insulator.

11. The generator of claim 1, further comprising an electrical conductor leading towards the electronic component from the lead connector block.

12. The generator of claim 1, wherein the electrical component is an ICD hybrid.

13. An header/feedthru assembly for an implantable pulse generator, the assembly comprising:
   a feedthru including an electrical insulator and a lead connector block, wherein the electrical insulator includes a header side and a pulse generator side opposite the header side, wherein the lead connector block is near the header side and comprises a plurality of spaced apart lead connectors mounted on the electrical insulator;
   a header including an electrically insulative barrier and a covering extending over the electrically insulative barrier, wherein the electrically insulative barrier extends over the header side, wherein the electrically insulative barrier defines a plurality of recesses configured to receive respective ones of the lead connectors therewithin.

14. The assembly of claim 13, wherein the electrically insulative barrier is molded, machined, or otherwise formed into existence as a distinct piece before being placed over the header face.

15. The assembly of claim 14, wherein the outer covering is molded or otherwise formed over the electrically insulative barrier subsequent to the electrically insulative barrier being placed over the header face.

16. The assembly of claim 14, wherein the electrically insulative barrier accounts for a greater volume of the header than the outer covering.

17. The assembly of claim 13, wherein the lead connector block extends from the header side.

* * * * *